United States Patent
Moody et al.

(10) Patent No.: US 11,879,626 B2
(45) Date of Patent: Jan. 23, 2024

(54) REDUCTION OF TEMPERATURE FROM HIGH POWER LED IN A MEDICAL SENSOR

(71) Applicant: Covidien LP, Mansfield, MA (US)

(72) Inventors: Derek L Moody, Longmont, CO (US);
Linden A. Reustle, Milliken, CO (US);
Sarah L. Hayman, Boulder, CO (US);
Jacob Dove, Lafayette, CO (US)

(73) Assignee: COVIDIEN LP, Mansfield, MA (US)

( * ) Notice: Subject to any disclaimer, the term of this patent is extended or adjusted under 35 U.S.C. 154(b) by 257 days.

(21) Appl. No.: 16/904,677

(22) Filed: Jun. 18, 2020

(65) Prior Publication Data

US 2021/0396379 A1 Dec. 23, 2021

(51) Int. Cl.
  *F21V 29/15* (2015.01)
  *A61B 5/00* (2006.01)
  *F21Y 115/10* (2016.01)
  *A61B 5/1455* (2006.01)

(52) U.S. Cl.
  CPC ............ *F21V 29/15* (2015.01); *A61B 5/6833* (2013.01); *A61B 5/14552* (2013.01); *A61B 5/6843* (2013.01); *F21Y 2115/10* (2016.08)

(58) Field of Classification Search
  CPC ..... F21V 29/15; A61B 5/6833; A61B 5/6843; A61B 2562/12; A61B 2562/146; A61B 5/6831; A61B 5/145; F21Y 2115/10
  See application file for complete search history.

(56) References Cited

U.S. PATENT DOCUMENTS

| | | | |
|---|---|---|---|
| 5,427,093 A | | 6/1995 | Ogawa et al. |
| 5,638,593 A | * | 6/1997 | Gerhardt ............ A61B 5/14552 356/41 |
| 5,891,026 A | * | 4/1999 | Wang ..................... A61B 5/411 600/479 |
| 2003/0109775 A1 | * | 6/2003 | O'Neil ................. A61B 5/6841 600/323 |
| 2006/0200017 A1 | | 9/2006 | Monfre et al. |
| 2010/0026995 A1 | | 2/2010 | Merritt et al. |
| 2014/0163342 A1 | * | 6/2014 | Shimuta ............. A61B 5/14552 600/323 |
| 2017/0071516 A1 | * | 3/2017 | Bhagat ................. A61B 5/0261 |

OTHER PUBLICATIONS

Lighting Manufacturer, "Best High Power LEDs", https://www.manufacturer.lighting/info/196/#:~:text=A%20high%20power%20LED%20is,or%20even%20thousands%20of%20lumens, (Year: 2020).*
International Application No. PCT/US2021/037725 International Search Report and Written Opinion dated Oct. 7, 2021, 11 pages.

* cited by examiner

*Primary Examiner* — Eric F Winakur
*Assistant Examiner* — Abid A Mustansir
(74) *Attorney, Agent, or Firm* — Fletcher Yoder, P.C.

(57) ABSTRACT

A patient monitoring sensor having a communication interface, through which the patient monitoring sensor can communicate with a monitor is provided. The patient monitoring sensor includes a light-emitting diode (LED) communicatively coupled to the communication interface and a detector, communicatively coupled to the communication interface, capable of detecting light. The patient monitoring sensor includes a layer of material is provided over the LED on the patient-side of the sensor to reduce transmission of heat therefrom to the skin of the patient.

20 Claims, 4 Drawing Sheets

REDUCTION OF TEMPERATURE FROM HIGH POWER LED IN A MEDICAL SENSOR

FIELD

The present disclosure relates generally to medical devices, and more particularly, to medical devices that monitor physiological parameters of a patient, such as pulse oximeters.

BACKGROUND

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient uses attenuation of light to determine physiological characteristics of a patient. This is used in pulse oximetry, and the devices built based upon pulse oximetry techniques. Light attenuation is also used for regional or cerebral oximetry. Oximetry may be used to measure various blood characteristics, such as the oxygen saturation of hemoglobin in blood or tissue, the volume of individual blood pulsations supplying the tissue, and/or the rate of blood pulsations corresponding to each heartbeat of a patient. The signals can lead to further physiological measurements, such as respiration rate, glucose levels or blood pressure.

One issue in such sensors relates to thermal transmission from emission sources. The present disclosure recognizes that use of higher power light emitting diodes (LEDs) in pulse oximetry sensors can cause adverse thermal effects with regard to patient skin, including discomfort adverse medical complications associated with prolonged usage.

Surface mount LEDs provide suitable open high-power options but also can provide issues with regard to skin contact pressure, being so narrow (length and width) as to create higher pressure on a patient's skin due to the smaller contact area, while at the same time transmitting excessive heat to the skin of the patient. This excessive temperature and higher pressure can cause discomfort, tissue necrosis or other problems.

Accordingly, pulse oximetry sensors avoiding such problems are needed in the art.

SUMMARY

The techniques of this disclosure generally relate to medical devices that monitor physiological parameters of a patient, such as pulse oximeters.

In one aspect, the present disclosure provides a patient monitoring sensor having a communication interface, through which the patient monitoring sensor can communicate with a monitor. The patient monitoring sensor also includes a light-emitting source, for example a light-emitting diode (LED), communicatively coupled to the communication interface and a detector, communicatively coupled to the communication interface, capable of detecting light. In exemplary embodiments, a layer of material is provided over the LED on the patient-side of the sensor to reduce transmission of heat to the skin of the patient.

In another aspect, the disclosure provides a patient monitoring sensor having a communication interface, through which the patient monitoring sensor can communicate with a monitor, wherein the sensor also includes a surface mount LED with an at least partially transparent disc or a ring positioned over at least a portion of the surface mount LED on the patent-side of the sensor.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector, communicatively coupled to the communication interface, capable of detecting light. The patient monitoring sensor further includes a layer of material provided over LED on the patient-side of the sensor to reduce transmission of heat to the skin of the patient.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The present disclosure recognizes that higher power light emitting diodes (LEDs) are beneficial, in combination with lower efficiency photodetectors to increase coupled optical efficiency (LED power×detector response) in order to increase signal to noise ratio (SNR) for hard to detect patients at corners of the population. Examples of hard to detect patients include, without limitation: babies with thick feet; adults with thick fingers; and dark pigment, among other cases providing high signal loss.

However, use of a higher power LED creates more heat, which poses a problem for a skin contacting sensor. Accordingly, exemplary aspects of the present disclosure provide a solution to reduce the temperature at the skin for high power LED that creates excessive heat when integrated into a skin contacting sensor.

Surface mount LEDs provide suitable open high-power options but also can provide issues with regard to skin contact pressure, being so narrow (length and width) as to create higher pressure on a patient's skin due to the smaller contact area, while at the same time transmitting excessive heat to the skin of the patient. This excessive temperature and higher pressure can cause discomfort, tissue necrosis or other problems.

Accordingly, the present disclosure describes a patient monitoring sensor that includes a material over the LED on the patient-side of the sensor. In exemplary embodiments, the covering material provides thermal resistance between the LED chip and the skin, increases the contact area to reduce excessive pressure and provides light transmission therethrough for the LED. In one exemplary aspect, the covering material comprises a disc that is at least partially transparent to light.

In another aspect, the disclosure provides a patient monitoring system, having a patient monitor coupled to a patient monitoring sensor. The patient monitoring sensor includes a communication interface, through which the patient monitoring sensor can communicate with the patient monitor. The patient monitoring sensor also includes a light-emitting diode (LED) communicatively coupled to the communication interface and a detector capable of detecting light. The patient monitoring sensor includes a thermally resistant covering material over the LED on the patient-side of the sensor.

Figure 1:
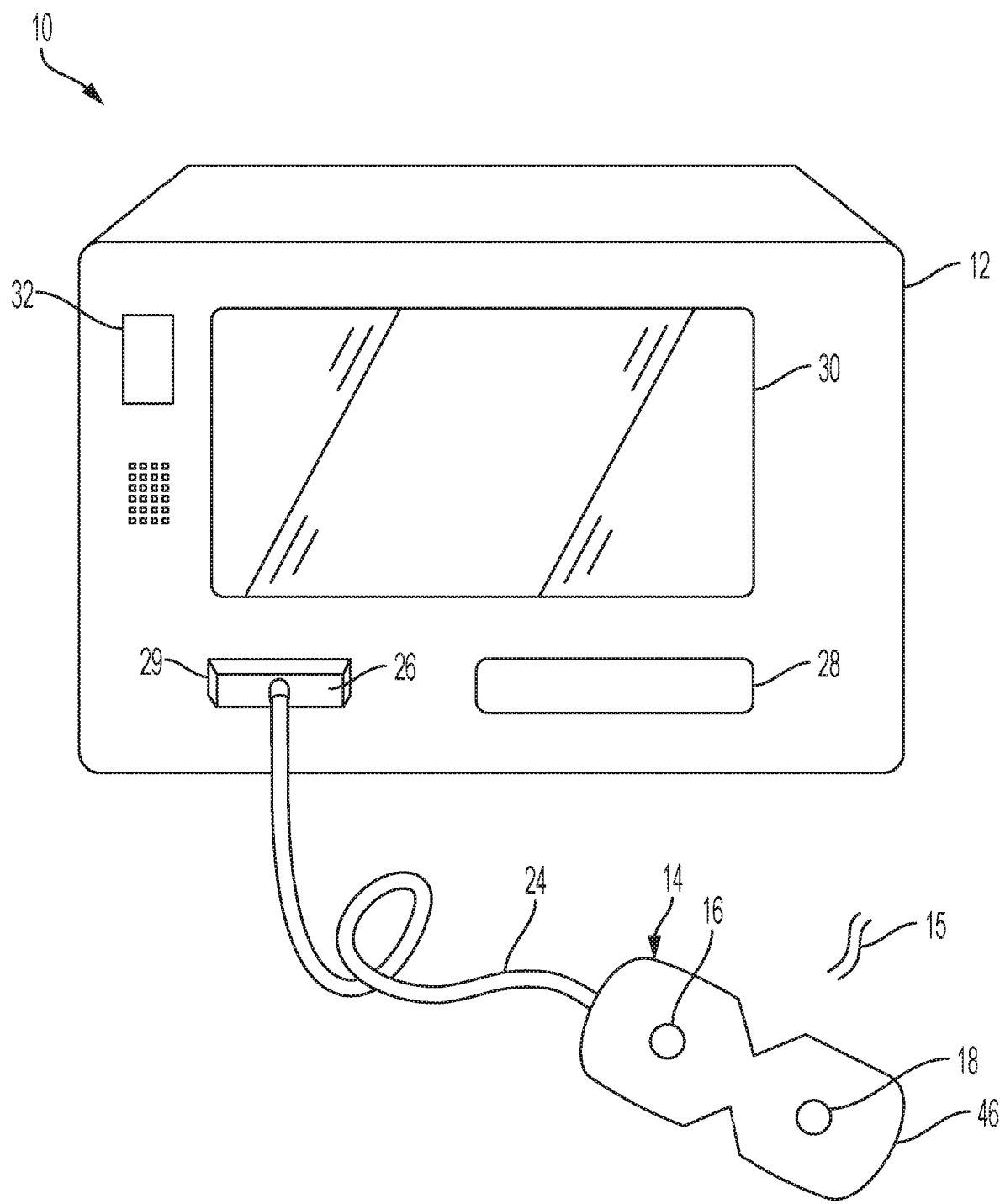
FIG. 1 illustrates a perspective view of an exemplary patient monitoring system including a patient monitor and a patient monitoring sensor, in accordance with an embodiment.

Referring now to FIG. 1, an embodiment of a patient monitoring system 10 that includes a patient monitor 12 and a sensor 14, such as a pulse oximetry sensor, to monitor physiological parameters of a patient is shown. By way of example, the sensor 14 may be a NELLCOR™, or INVOS™ sensor available from Medtronic (Boulder, Colorado), or another type of oximetry sensor. Although the depicted embodiments relate to sensors for use on a patient's fingertip, toe, or earlobe, it should be understood that, in certain embodiments, the features of the sensor 14 as provided herein may be incorporated into sensors for use on other tissue locations, such as the forehead and/or temple, the heel, stomach, chest, back, or any other appropriate measurement site.

In the embodiment of FIG. 1, the sensor 14 is a pulse oximetry sensor that includes one or more emitters 16 and one or more detectors 18. For pulse oximetry applications, the emitter 16 transmits at least two wavelengths of light (e.g., red and/or infrared (IR)) into a tissue of the patient. For other applications, the emitter 16 may transmit 3, 4, or 5 or more wavelengths of light into the tissue of a patient. The detector 18 is a photodetector selected to receive light in the range of wavelengths emitted from the emitter 16, after the light has passed through the tissue. Additionally, the emitter 16 and the detector 18 may operate in various modes (e.g., reflectance or transmission). In certain embodiments, the sensor 14 includes sensing components in addition to, or instead of, the emitter 16 and the detector 18. For example, in one embodiment, the sensor 14 may include one or more actively powered electrodes (e.g., four electrodes) to obtain an electroencephalography signal.

The sensor 14 also includes a sensor body 46 to house or carry the components of the sensor 14. The body 46 includes a backing, or liner, provided around the emitter 16 and the detector 18, as well as an adhesive layer (not shown) on the patient side. The sensor 14 may be reusable (such as a durable plastic clip sensor), disposable (such as an adhesive sensor including a bandage/liner materials), or partially reusable and partially disposable.

In the embodiment shown, the sensor 14 is communicatively coupled to the patient monitor 12. In certain embodiments, the sensor 14 may include a wireless module configured to establish a wireless communication 15 with the patient monitor 12 using any suitable wireless standard. For example, the sensor 14 may include a transceiver that enables wireless signals to be transmitted to and received from an external device (e.g., the patient monitor 12, a charging device, etc.). The transceiver may establish wireless communication 15 with a transceiver of the patient monitor 12 using any suitable protocol. For example, the transceiver may be configured to transmit signals using one or more of the ZigBee standard, 802.15.4x standards WirelessHART standard, Bluetooth standard, IEEE 802.11x standards, or MiWi standard. Additionally, the transceiver may transmit a raw digitized detector signal, a processed digitized detector signal, and/or a calculated physiological parameter, as well as any data that may be stored in the sensor, such as data relating to wavelengths of the emitters 16, or data relating to input specification for the emitters 16, as discussed below. Additionally, or alternatively, the emitters 16 and detectors 18 of the sensor 14 may be coupled to the patient monitor 12 via a cable 24 through a plug 26 (e.g., a connector having one or more conductors) coupled to a sensor port 29 of the monitor. In certain embodiments, the sensor 14 is configured to operate in both a wireless mode and a wired mode. Accordingly, in certain embodiments, the cable 24 is removably attached to the sensor 14 such that the sensor 14 can be detached from the cable to increase the patient's range of motion while wearing the sensor 14.

The patient monitor 12 is configured to calculate physiological parameters of the patient relating to the physiological signal received from the sensor 14. For example, the patient monitor 12 may include a processor configured to calculate the patient's arterial blood oxygen saturation, tissue oxygen saturation, pulse rate, respiration rate, blood pressure, blood pressure characteristic measure, autoregulation status, brain activity, and/or any other suitable physiological characteristics. Additionally, the patient monitor 12 may include a monitor display 30 configured to display information regarding the physiological parameters, information about the system (e.g., instructions for disinfecting and/or charging the sensor 14), and/or alarm indications. The patient monitor 12 may include various input components 32, such as knobs, switches, keys and keypads, buttons, etc., to provide for operation and configuration of the patient monitor 12. The patient monitor 12 may also display information related to alarms, monitor settings, and/or signal quality via one or more indicator lights and/or one or more speakers or audible indicators. The patient monitor 12 may also include an upgrade slot 28, in which additional modules can be inserted so that the patient monitor 12 can measure and display additional physiological parameters.

Because the sensor 14 may be configured to operate in a wireless mode and, in certain embodiments, may not receive power from the patient monitor 12 while operating in the wireless mode, the sensor 14 may include a battery to provide power to the components of the sensor 14 (e.g., the emitter 16 and the detector 18). In certain embodiments, the battery may be a rechargeable battery such as, for example, a lithium ion, lithium polymer, nickel-metal hydride, or nickel-cadmium battery. However, any suitable power source may be utilized, such as, one or more capacitors and/or an energy harvesting power supply (e.g., a motion generated energy harvesting device, thermoelectric generated energy harvesting device, or similar devices).

As noted above, in an embodiment, the patient monitor 12 is a pulse oximetry monitor and the sensor 14 is a pulse oximetry sensor. The sensor 14 may be placed at a site on a patient with pulsatile arterial flow, typically a fingertip, toe, forehead or earlobe, or in the case of a neonate, across a foot. Additional suitable sensor locations include, without limitation, the neck to monitor carotid artery pulsatile flow, the wrist to monitor radial artery pulsatile flow, the inside of a patient's thigh to monitor femoral artery pulsatile flow, the ankle to monitor tibial artery pulsatile flow, and around or in front of the ear. The patient monitoring system 10 may include sensors 14 at multiple locations. The emitter 16 emits light which passes through the blood perfused tissue, and the detector 18 photoelectrically senses the amount of light reflected or transmitted by the tissue. The patient monitoring system 10 measures the intensity of light that is received at the detector 18 as a function of time.

A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The amount of light detected or absorbed may then be used to calculate any of a number of physiological parameters, including oxygen saturation (the saturation of oxygen in pulsatile blood, SpO2), an amount of a blood constituent (e.g., oxyhemoglobin), as well as a physiological rate (e.g., pulse rate or respiration rate) and when each individual pulse or breath occurs. For SpO2, red and infrared (IR) wavelengths may be used because it has been observed that highly oxygenated blood will absorb relatively less Red light and more IR light than blood with a lower oxygen saturation. By comparing the intensities of two wavelengths at different points in the pulse cycle, it is possible to estimate the blood oxygen saturation of hemoglobin in arterial blood, such as from empirical data that may be indexed by values of a ratio, a lookup table, and/or from curve fitting and/or other interpolative techniques.

Figure 2:
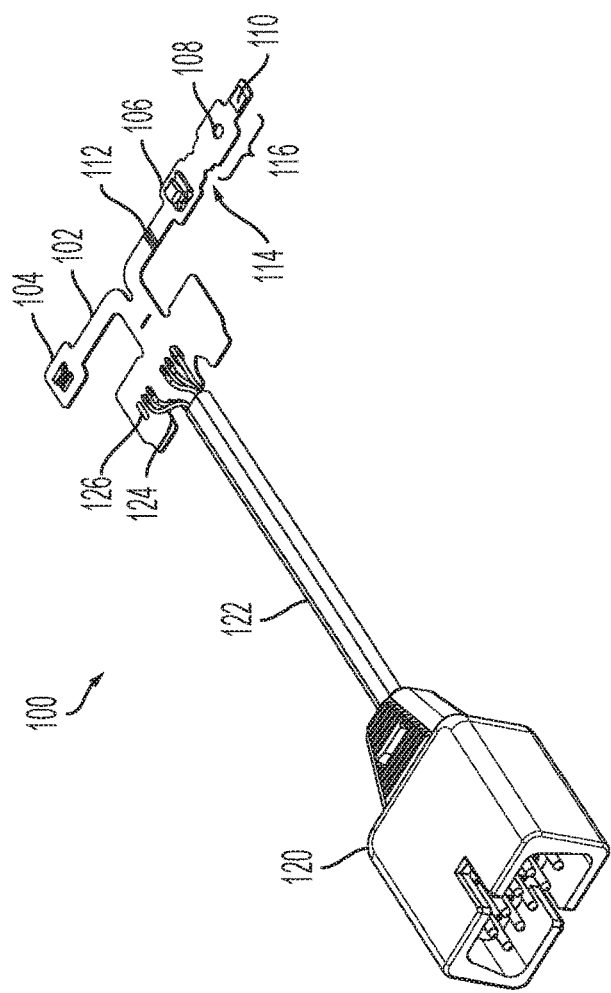
FIG. 2 illustrates a perspective view of an exemplary patient monitoring sensor, in accordance with an embodiment.

Referring now to FIG. 2, an embodiment of a patient monitoring sensor 100 in accordance with an embodiment is shown. As may be seen, the shape or profile of various components may vary. The sensor 100 includes a body 102 that includes a flexible circuit. The sensor 100 includes an LED 104 (for example, a surface mount LED) and a detector 106 disposed on the body 102 of the sensor 100.

In exemplary aspects of the present disclosure, the LED is a high-power LED configured to overcome high signal loss in patients having conditions providing such signal loss, such as thick anatomy, dark pigment, etc. In further exemplary embodiments, such a high-power LED is used in conjunction with a lower efficiency photodetector to increase coupled optical efficiency in order to increase SNR for such hard to detect patients. Photocurrent output scales linearly with the area of the detector. Use of a high-powered LED allows for use of a smaller detector.

While any number of exemplary sensor designs are contemplated herein, in the illustrated exemplary embodiment, the body 100 includes a flap portion 116 that includes an aperture 108. The flap portion 116 is configured to be folded at a hinge portion 114 such that the aperture 108 overlaps the detector 106 to allow light to pass through. In one embodiment, the flap portion 116 includes an adhesive 110 that is used to secure the flap portion 116 to the body 102 after the flap portion 116 is folded at the hinge portion 114.

The sensor 100 includes a plug 120 that is configured to be connected to a patient monitoring system, such as the one shown in FIG. 1. The sensor 100 also includes a cable 122 that connects the plug 120 to the body 102 of the sensor 100. The cable 122 includes a plurality of wires 124 that connect various parts of the plug 120 to terminals 126 disposed on the body 102. The flexible circuit is disposed in the body 102 and connects the terminals 126 to the LED 104 and the detector 106. In addition, one of the terminals 126 connect a ground wire to the flexible circuit.

In exemplary embodiments, the aperture 108 is configured to provide electrical shielding to the detector 106. In exemplary embodiments, aperture 108 also limits the amount of light that is received by the detector 106 to prevent saturation of the detector. In exemplary embodiments, the configuration of the aperture 108, i.e., a number, shape, and size of the openings that define the aperture 108 can vary. As illustrated, in one embodiment, the aperture 108 includes a single round opening. In other embodiments, the aperture 108 can include one or more openings that have various shapes and sizes. The configuration of the aperture 108 is selected to provide electrical shielding for the detector 106 and/or control the amount of light that is received by the detector 106. In exemplary embodiments, the body 102 includes a visual indicator 112 that is used to assure proper alignment of the flap portion 116 when folded at the hinge portion 114. Further, the shape of the material of the flap portion 116 around the aperture 108 can vary, while at the same time increasing the surface area around the detector to reduce the contact pressure from the detector on the skin.

Figure 3:
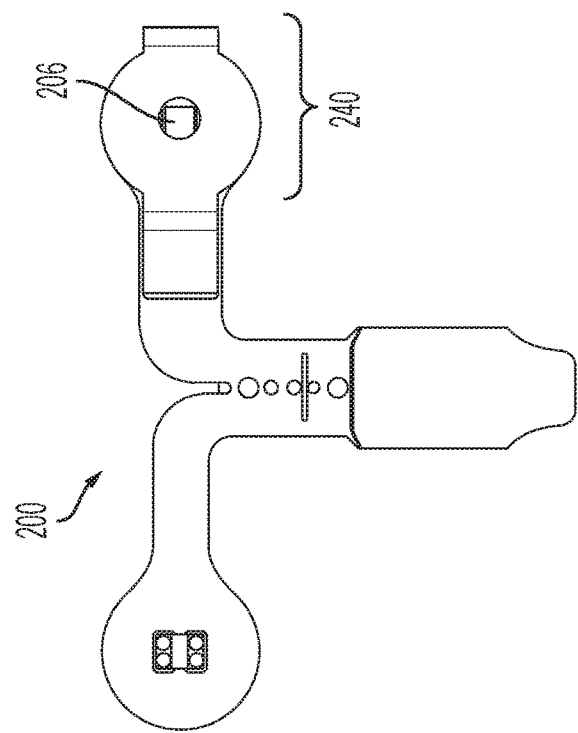
FIG. 3 illustrates a schematic view of an exemplary patient monitoring sensor, in accordance with an embodiment.

Referring now to FIG. 3, a patient monitoring sensor 200 in accordance with an embodiment is shown. In exemplary embodiments, a faraday cage 240 is formed around the detector 206 by folding the flap portion 116 over a portion of the body 102 of the sensor 200. In exemplary embodiments, one or more flap portions may be used to cover any additional desired sensor structure, for example also including over the LED side to provide an air gap between a hot LED and patient contacting adhesive (further increasing thermal resistance).

In further exemplary embodiments, materials for the sensor and bandage generally comprise hydrophobic materials, for example including a polyester backing and a silicone patient adhesive.

Figure 4:
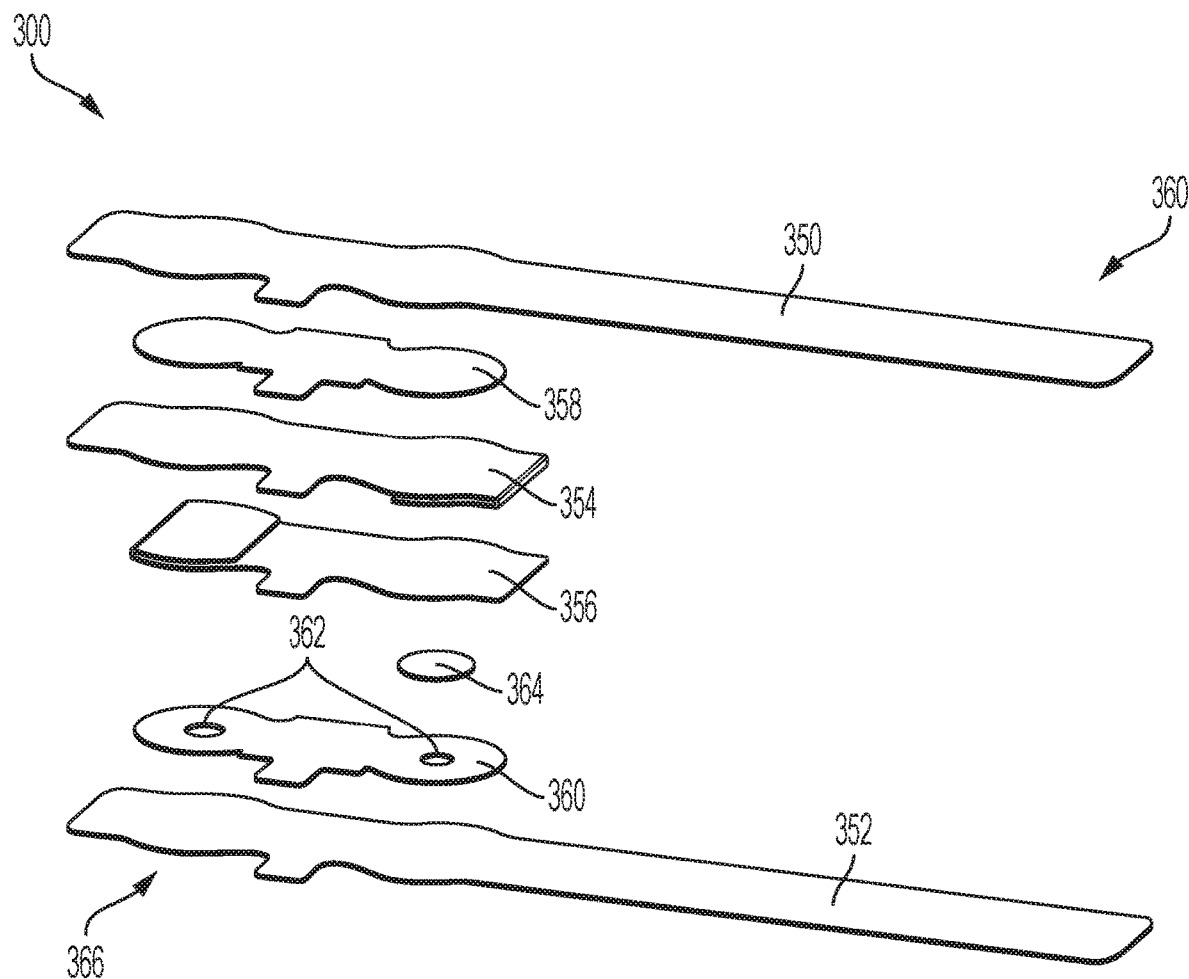
FIG. 4 illustrates a layered schematic view of an exemplary patient monitoring sensor bandage, in accordance with an embodiment.

FIG. 4 illustrates an expanded perspective view generally at 300 of an exemplary layered body/bandage configuration for a pulse oximeter sensor. The configuration includes: an upper bandage 350; an exemplary bottom tape/patient adhesive 352; exemplary top internal liner 354 and bottom internal liner 356, which in exemplary embodiments are discarded during sensor assembly, allowing the bandage to open like a leaflet to insert the flex circuit of FIGS. 2 and 3 into the bandage; a top light blocking layer 358, for example a metallized tape; a bottom light blocking layer 360, for example a metallized tape with holes 362 configured to allow light to shine through; and a disc 364, comprising for example a polyethylene material, configured to reduce pressure from the LED on the patient. In exemplary embodiments, bottom tape 352 comprises an adhesive layer with a release liner 366 on the patient facing side of tape 352.

Figure 5:
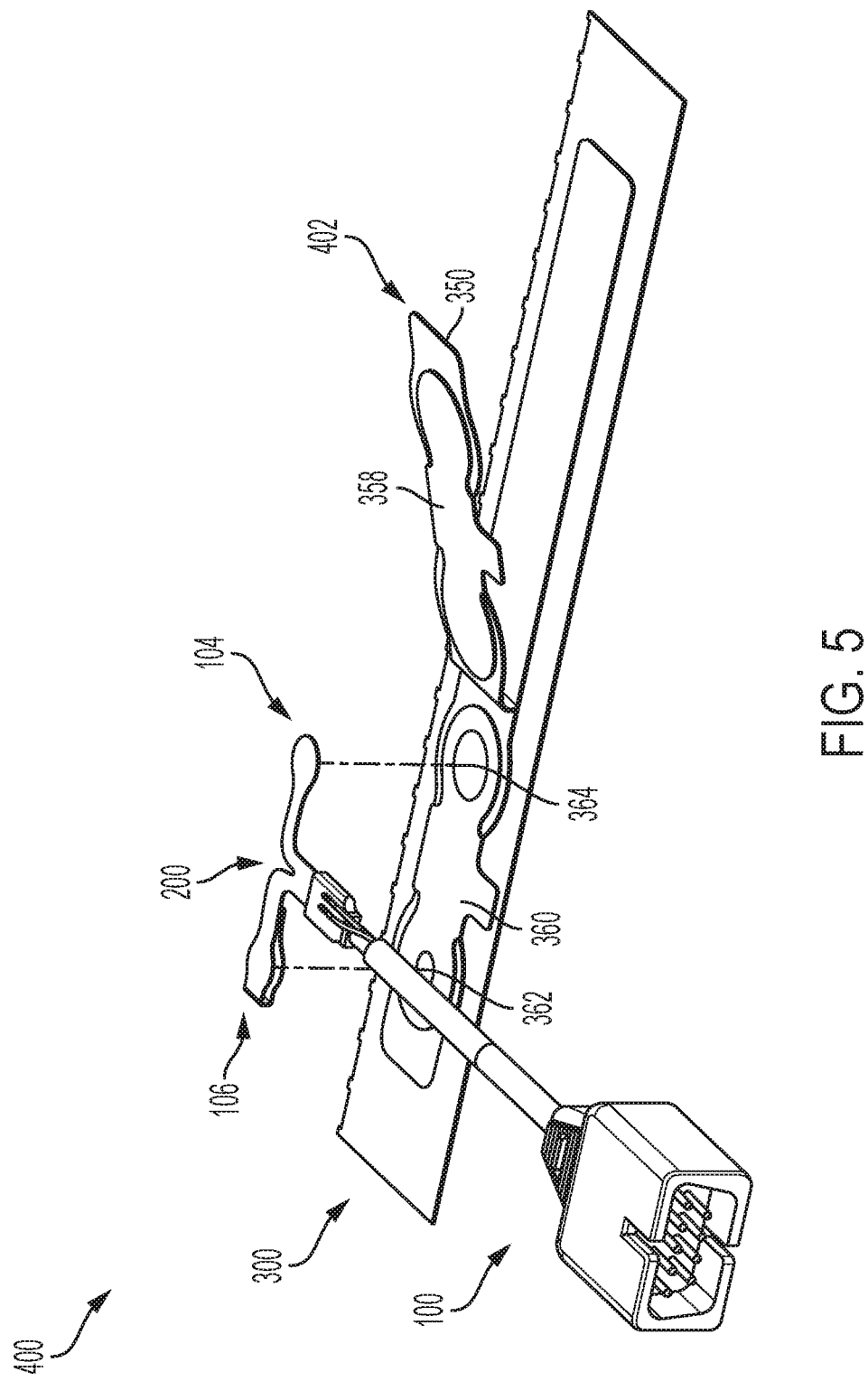
FIG. 5 illustrates a perspective view of an exemplary sensor assembly.

FIG. 5 illustrates a perspective view of exemplary assembly of the flex circuit 200 of FIGS. 2 and 3 into the bandage 300, with internal liners 354, 356 removed to allow positioning of the flex circuit 200 into the bandage, between the light blocking layers 358, 360. As is shown, detector 106 is positioned over hole 362. LED 104 is positioned over disc 364 (which is positioned over another hole 362 (not shown in FIG. 5)). Rapid assembly is facilitated by removable liners 354, 356, as well as the upper bandage 350 and light blocking layer 358 acting as a foldable leaflet 402, the exemplary bandage construction provided as a sub-assembly configured to provide high-volume, fast and repeatable production of sensor assemblies.

Exemplary materials for backing or other material includes plastics, such as polypropylene (PP), polyester (PES), polyethylene (PE), urethanes, silicone, or the like. Additionally, various layers of the device may be constructed of one or more hydrophobic materials. Bandage, backing and additional possible layers may comprise a variety of thicknesses.

In exemplary embodiments, disc 364 is a thin disc (e.g, 0.1 millimeter (mm) polyethylene, which is semi-transparent and is operative to maintain the light transmission from the LED through the PET) inserted in or integral to bandage between the LED and the patient-side of the sensor, e.g., to reduce contact pressure on the skin.

Other thicknesses of materials are also contemplated, for example 0.08 mm-0.12 mm; 0.1 mm-0.15 mm, etc. Thickness of the disc may be selected to be thin enough so as not to increase the profile of the sensor (not increase pressure), but also thick enough to provide thermal resistance. Also, because thermal resistance is linearly related to thickness, variation in thicknesses of the material itself is contemplated. In exemplary embodiments, thicker material in center of disc may be provided relative to edge thickness to minimize disc thickness at edges due to pressure. Low thermal conductivity materials (such as PET) are suitable since they create high thermal resistance. Further materials such as PET can be manufactured in sheets of thin film that are at least partially transparent and can be die cut easily.

In exemplary embodiments, the sensor is configured utilizing materials having a thickness configured to keep the temperature at the hottest point on the sensor surface (which is the patient adhesive closest to the LED) at or lower than 41 degrees Centigrade, assuming a patient is at 35 degrees Centigrade. Such configuration accounts for the heat of the LED and heat loss: $R=(T\_LED-41)/q$, where T_LED is the temperature of the LED and q=heat loss from the LED (W). Heat loss can be estimated as q=electrical power−optical power.

In FIGS. 4 and 5, the disc 364 is inserted between the LED and the bottom of the sensor bandage to provide thermal resistance. Additionally, such disc can propagate the force from the LED to a wider area.

In exemplary embodiments, a PET disc 364 is converted with an acrylic adhesive on one side and die cut into an 8 millimeter (mm) disc (though ranges of sizes are contemplated, e.g., 5-12 mm, 6-10 mm, 7-9 mm, etc.) that is adhered to the bottom tape of the sensor. In exemplary embodiments, the bottom tape (352 in FIG. 4) has an adhesive facing toward the disc 364, which adheres the disc in place.

In further exemplary embodiments, the LED (104 in FIG. 2) is soldered to the flex circuit (200 in FIG. 3), which is placed on top of the adhesive side of the disc 364 (see FIG. 5). The adhesive of the disc 364 secures the disc in place relative to the LED 104.

Thus, according to example embodiments described herein, the disc (or other alternative structure) reduces thermal transmission from the LED when placed over the LED, resulting in a sensor that does not transmit excessive heat to the skin of a patient. As we have noted, while exemplary embodiments describe a disc, alternate embodiments contemplate other shapes, for example square shapes, rectangular shapes, etc.

One or more specific embodiments of the present techniques will be described below. In an effort to provide a concise description of these embodiments, not all features of an actual implementation are described in the specification. It should be appreciated that in the development of any such actual implementation, numerous implementation-specific decisions must be made, which may vary from one implementation to another.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A patient monitoring sensor, comprising:
a communication interface, through which the patient monitoring sensor can communicate with a monitor;
a light-emitting diode (LED) communicatively coupled to the communication interface;
a detector, communicatively coupled to the communication interface, capable of detecting light;
a layer of material provided over the LED and facing a patient-side of the sensor, without a corresponding layer of material provided over the detector on the patient-side of the sensor, wherein the layer of material is configured to reduce the thermal transmission of the LED to the patient-side of the sensor;
a patient-side layer; and
a bandage folded over the patient-side layer and securing the layer of material and the LED between the bandage and the patient-side layer.

2. The patient monitoring sensor of claim 1, wherein the layer of material comprises a material having low thermal conductivity.

3. The patient monitoring sensor of claim 2, wherein the layer of material is at least partially transparent in a portion between the LED and the patient-side of the sensor.

4. The patient monitoring sensor of claim 2, wherein the layer of material comprises a disc provided between the LED and the patient-side of the sensor.

5. The patient monitoring sensor of claim 4, wherein the layer of material comprises polyethylene.

6. The patient monitoring sensor of claim 5, wherein the disc has a thickness of about 0.08 millimeters to about 0.12 millimeters.

7. The patient monitoring sensor of claim 6, wherein the thickness of the disc is approximately 0.1 millimeter, and wherein the disc has a diameter of approximately eight millimeters.

8. The patient monitoring sensor of claim 1, wherein the LED is a high power LED.

9. The patent monitoring sensor of claim 8, wherein the high power LED is coupled to a low efficiency detector.

10. The patient monitoring sensor of claim 9, a wherein the patient-side layer comprises a tape adhered to the layer of material, wherein the layer of material comprises as a disc provided between the LED and the patient-side of the sensor.

11. A method for making a patient monitoring system, comprising:
coupling a light-emitting diode (LED) communicatively to a communication interface;
coupling a detector capable of detecting light communicatively to a communication interface;

positioning a layer of material over the LED and facing a patient-side of the sensor, without a corresponding layer of material provided over the detector on the patient-side of the sensor, wherein the layer of material is configured to reduce the thermal transmission of the LED to the patient-side of the sensor;

positioning a patient-side layer over the layer of material; and folding a bandage over the patient-side layer to secure the layer of material and the LED between the bandage and the patient-side layer.

12. The method of claim 11, wherein the layer of material comprises a material having low thermal conductivity.

13. The method of claim 12, wherein the layer of material is at least partially transparent in a portion between the LED and the patient-side of the sensor.

14. The method of claim 12, wherein the layer of material comprises a disc provided between the LED and the patient-side of the sensor.

15. The method of claim 14, wherein the layer of material comprises polyethylene.

16. The method of claim 15, wherein the disc has a thickness of about 0.08 millimeters to about 0.12 millimeters.

17. The method of claim 16, wherein the thickness of the disc is approximately one millimeter, and wherein the disc has a diameter of approximately eight millimeters.

18. The method of claim 11, wherein the LED is a high power LED.

19. The method of claim 18, wherein the high power LED is coupled to a low efficiency detector.

20. The method of claim 19, wherein the patient-side layer comprises a tape adhered to the layer of material, and wherein the layer of material comprises a disc provided between the LED and the patient-side of the sensor.

* * * * *